United States Patent
Akeno et al.

[11] Patent Number: 6,127,018
[45] Date of Patent: Oct. 3, 2000

[54] SYNTHETIC RESIN SKIDPROOF DEVICE

[75] Inventors: Mitsuru Akeno; Ryuichi Murasaki, both of Toyama, Japan

[73] Assignee: YKK Corporation, Tokyo, Japan

[21] Appl. No.: 09/037,974

[22] Filed: Mar. 9, 1998

[30] Foreign Application Priority Data

Mar. 10, 1997 [JP] Japan ...................................... 9-054987

[51] Int. Cl.⁷ .............................. A44B 18/00; B32B 3/06
[52] U.S. Cl. .............................. 428/100; 24/442; 24/452; 428/99; 428/120
[58] Field of Search .............................. 24/442, 452, 450, 24/340, 446; 428/99, 100, 120

[56] References Cited

U.S. PATENT DOCUMENTS

| | | | |
|---|---|---|---|
| 3,708,833 | 1/1973 | Ribich | 24/204 |
| 5,067,210 | 11/1991 | Kayaki | 24/452 |
| 5,685,050 | 11/1997 | Murasaki | 24/449 |

*Primary Examiner*—Ellis Robinson
*Assistant Examiner*—Alicia Chevalier
*Attorney, Agent, or Firm*—Hill & Simpson

[57] ABSTRACT

In a skidproof device continuously molded of synthetic resin and adapted to be used with a disposable companion sheet product, a multiplicity of skidproof engaging elements are molded on the front surface of a substrate sheet for mating with engaging elements of the companion sheet product. Each skidproof engaging element is composed of a single stem, at least two necks branched and gently sloping upwardly from an upper end of the stem, and at least two heads extending one from an upper end of each neck with an upward gentle slope. Each head has on its top an upwardly convex arcuate surface. Having the differently directed engaging elements, the front surface of this device is smooth in touch and non-directive to give adequate resistance to skidding.

8 Claims, 4 Drawing Sheets

SYNTHETIC RESIN SKIDPROOF DEVICE

BACKGROUND OF THE INVENTION

1. Field of the Invention

This invention relates to a skidproof device which is composed of a substrate sheet and a multiplicity of engaging elements continuously molded by injection using synthetic resin, and more particularly to a synthetic resin skidproof device in which the engaging elements are small in size and are engaged with a companion sheet product reliably to prevent the sheet from skidding and which is adequately resistant to repeating engaging and disengaging operations several times and is therefore suitable for use in a paper diaper, a sanitary pad or the like.

2. Description of the Related Art

A molded type skidproof surface fastener composed of a substrate sheet and a multiplicity of hook-shaped engaging elements integrally molded continuously by extrusion using synthetic resin is used as attached to a diaper for preventing various kinds of disposable sanitary pads made of paper or non-woven cloth from skidding. This prior art is exemplified by Japanese Utility Model Laid-Open Publication No. Hei 4-128611.

The molded surface fastener disclosed in the above-named publication comprises a substrate sheet, and a multiplicity of holding and engaging elements standing on the front surface of the substrate sheet; and as a typical form, each engaging element has a usual inverted J-shape hook and a taper head which are branched from the upper end of a single stem, the taper head rising upright to a position higher than the top of the hook. If the surface fastener is pressed against a companion sanitary pad for example, the taper heads penetrate into the pad and, at the same time, the hooks engage loops projecting from the front surface of the pad. The taper heads prevent the pad from skidding, while the hooks hold the pad in place.

However, in the case that the molded surface fastener is attached to a diaper or the like, it often comes into direct contact with the skin of the user. And thus the taper heads of the above-described holding and engaging elements inevitably give such a strong itchy touch as to cause a rough skin when the taper heads contact with the skin.

In addition, since the hook and the taper head are branched by an acute angle, the holding and engaging element tends to tear from the branching portion when it is pressed toward the substrate sheet which makes repeated use impossible.

SUMMARY OF THE INVENTION

It is therefore an object of this invention to provide a skidproof device which is excellent in touch and has a new durable structure.

According to the invention, the above object is accomplished by a synthetic resin skidproof device comprising: a substrate sheet; and a multiplicity of skidproof engaging elements molded on a front surface of the substrate sheet and adapted to be mated with a companion sheet product. Each of the skidproof engaging elements is composed of a single stem, at least two necks branched and gently sloping upwardly from an upper end of the stem, and at least two heads extending one from an upper end of each of the necks with an upward gentle slope, each of the heads having on its top an upwardly convex arcuate surface.

Basically the skidproof device has no necessity of positively engaging the companion sheet product. For example, in the case that the sheet product is a fiber product, such as non-woven cloth, paper or woven or knit cloth, when such sheet product is pressed against the skidproof device, the heads of the engaging elements are easily bent about the necks to give an effective skidproof function because of the friction. Further, if the sheet product has on its surface small pile or loops, the heads penetrate into the loops to make the skidproof function more efficient.

Preferably, each of said skidproof engaging elements has at a branching portion of said necks a concave arcuate surface, and the center line of each of the heads is slightly curved upwardly. A thickness $W_1$ of the stem of each skidproof engaging element in a direction of branching of the necks is 0.3–2.0 mm, a thickness $W_2$ of necks of each skidproof engaging element in a direction perpendicular to the direction of bending is 0.1–1.5 mm, a height H between the front surface of the substrate sheet and an uppermost point O of each head is 0.2–2.0 mm, and a distance $L_1$ between respective outermost end surfaces of the heads branched in opposite directions from the same stem is 0.4–3.8 mm. Further preferably, the number of the heads of each skidproof engaging element is two which are directed in opposite directions. And a radius $R_1$ of curvature of the arcuate surface of the top of each head is at least 0.04 mm, a radius $R_2$ of curvature of the arcuate surface of the branching portion of the necks of each skidproof engaging element is at least 0.02 mm, at least one local portion of each said head is smaller in cross-sectional area than the remaining portion, and an angle $\theta$ between the necks branched oppositely from the same stem is 30°–120°.

With this arrangement, partly since the top of the individual head has an arcuate surface and partly since the center line of the individual head is arcuate, it is possible to make the entire front surface of the skidproof device substantially smooth eliminating an itchy feeling so that the skin can be prevented from being rough. Also, since the branching portion of the necks of each engaging element has a concave arcuate surface, it is possible to prevent the engaging element from being torn at the branching portion even when the engaging element is pressed to deform, thus causing an adequate degree of durability to repeated use. With the individual parameters of the engaging elements set in the above-mentioned range, it is possible to expand the application of the skidproof device to various kinds of sheet products, such as diapers, sanitary pads and sole-in-shoe pads, as well as other products such as interior ornaments.

According to an additional feature of the invention, in which the substrate sheet has in the front surface a multiplicity of recesses so that the skidproof engaging elements rise upwardly from bottom surfaces of the recesses, it is possible to increase the actual height of the engaging elements by adding the depth of the recesses to the apparent height of the engaging elements, namely, the distance between the entire front surface, except the recesses, of the substrate sheet and the top surfaces of the heads.

With the recesses in the front surface of the substrate sheet, even if the apparent thickness of the substrate sheet is kept unchanged, it is possible to improve the softness of the substrate sheet remarkably and to peel the molded skidproof device from the molding die stably without causing the substrate sheet to inadvertently expand or tear. As a result, the substrate sheet of the molded skidproof device is free from puckering and a high quality product adequately durable to repeated use can be obtained. Further, partly since the presence of the necks increases the flexibility of the heads and partly since the apparent height of the stems above the entire front surface except the recesses of the substrate sheet is relatively low, the individual stems are so stable in shape as not to fall down during engaging.

The foregoing skidproof device may be continuously manufactured as follows. Molten synthetic resin continuously injected from an extrusion nozzle under a predetermined resin pressure is continuously pressed against the circumferential surface of a rotating die wheel to mold a substrate sheet along the circumferential surface of the die wheel from part of the molten synthetic resin and, at the same time, to fill a multiplicity of engaging-element-forming cavities on the circumferential surface of the rotating die wheel successively with the molten synthetic resin to mold a multiplicity of skidproof engaging elements so that the substrate sheet and the engaging elements are simultaneously molded continuously. While it revolves about a substantially half of the circumferential surface of the die wheel, the molded skid device is positively cooled from the inside of the die wheel by a water cooling jacket and passes in a cooling water tank, in which low-temperature cooling water circulates, so that the molded skidproof device is quickly cooled to become quickly solidified. Since the molded skidproof starts its solidification prior to progressing its crystallization because of this quick cooling, it is possible to make the substrate sheet and the engaging elements wholly adequately soft. Therefore the resulting skidproof device is particularly suitable for use in underwear, diapers, sanitary pads, bedclothes or the like, which require adequate softness.

When the solidified substrate sheet is drawn from the die wheel by take-up rollers, the individual engaging elements cooled and solidified in the engaging-element-forming cavities are smoothly removed off the cavities while being resiliently deformed into a straight form. More particularly since opposed rear surfaces of the opposite necks of each engaging element gently slant upwardly in diverging directions from the center of the upper end of the stem, the thickness of the heads in their branching direction is less than about half of the thickness of the stem in the same direction, so that removing of the engaging elements off the cavities is facilitated.

DETAILED DESCRIPTION OF THE PREFERRED EMBODIMENTS

Figure 1:
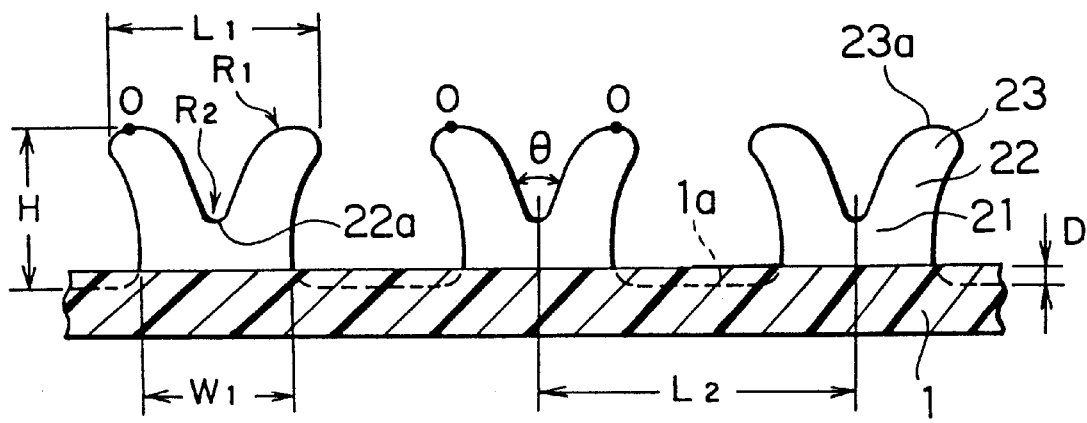
FIG. 1 is a fragmentary side view, partly in cross section, of a skidproof device according to a first embodiment of this invention.

Various preferred embodiments of this invention will now be described in detail with reference to the accompanying drawings. FIG. 1 is a fragmentary side view of a synthetic resin skidproof device according to a first embodiment of the invention, FIG. 2 is a fragmentary front view of the skidproof device, and FIG. 3 is a fragmentary perspective view of the skidproof device.

Figure 2:
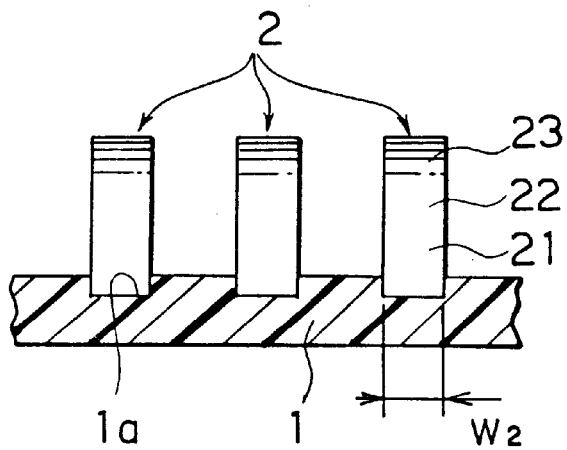
FIG. 2 is a fragmentary front view of FIG. 1.
Figure 3:
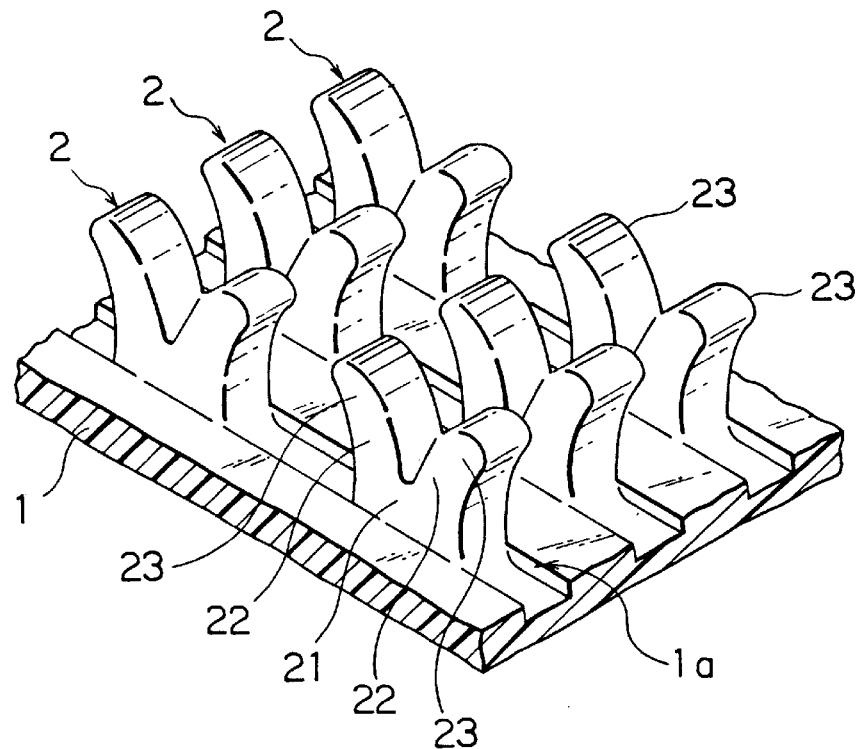
FIG. 3 is a fragmentary perspective view of the skidproof device of the first embodiment.

As shown in FIGS. 1–3, the synthetic resin skidproof device of the first embodiment comprises a substrate sheet 1 and a multiplicity of skidproof engaging elements (hereinafter called the engaging elements) 2 molded on a front surface of the substrate sheet 1, each engaging element 2 being composed of a stem 21 rising upright from the front surface of the substrate sheet, two necks 22 branched from the upper end of the stem 21 with respect to each other by a predetermined angle θ, and two gently sloping straight heads 23 in which one head 23 projects from each of the necks 22. Alternatively, three or more heads 23 may extend in different directions, preferably radially outwardly, from a single stem 21 in order not to make the skidproof feature of the individual engaging element 2 directive.

In this embodiment, the substrate sheet 1 has in the front surface a number of continuous straight recesses 1a extending one along each row of the engaging elements 2. The stems 21 of the engaging elements 2 in each row are arranged at a predetermined pitch and rise upright from the bottom surface of the corresponding recess 1a. Opposite side surfaces of the individual stem 21 are integral with side walls of the recess 1a and, as a result, a subdivided recess 1a is defined between each pair of adjacent stems 21 in the same row. According to the illustrated example, the heads 23 of the engaging elements 21 in the same row are all directed longitudinally of the row and a multiplicity of such engaging element rows are arranged in parallel. The recesses 1a should by no means limited to this illustrated shape, and those in the same row of engaging elements 2 may be completely independent from one another. In another alternative form, the subdivided recesses 1a in adjacent rows may be arranged in a meandering pattern.

Figure 4:
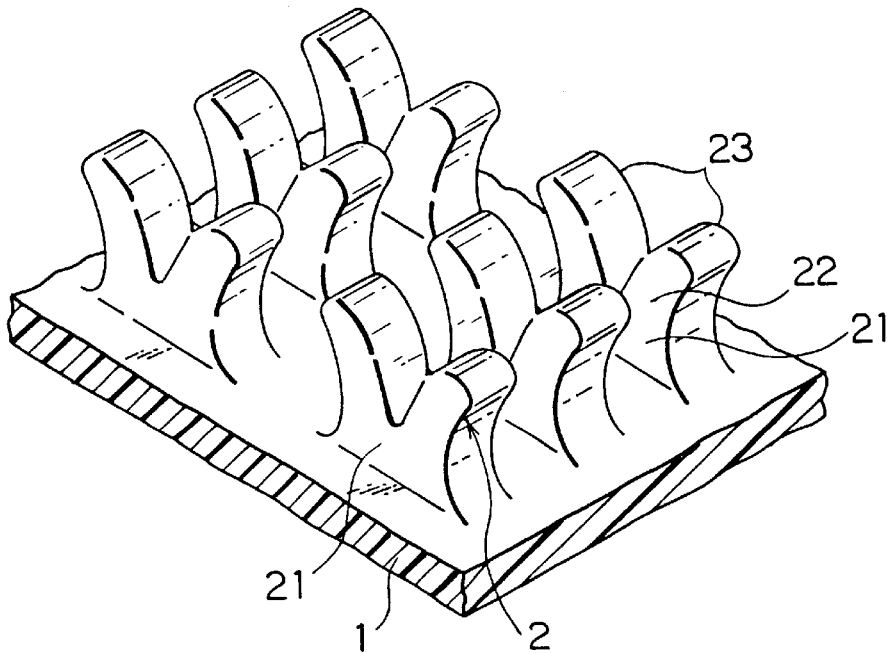
FIG. 4 is a fragmentary perspective view similar to FIG. 3, but showing another skidproof device according to a second embodiment.

With the recesses 1a in the front surface of the substrate sheet, even if the apparent thickness of the substrate sheet is kept unchanged, it is possible to improve the softness of the substrate sheet remarkably and, with the help of the above-described shape of the engaging element 2, also possible to peel the molded skidproof device from the molding die stably without causing the substrate sheet to inadvertently expand or tear. Consequently, the substrate sheet 1 of the molded skidproof device is free from puckering and a high quality product adequately durable to repeated use can be obtained. Alternatively, the substrate sheet 1 may have an entirely flat surface devoid of any recess 1a according to a second embodiment shown in FIG. 4.

As a characteristic feature of the engaging element 2 of this invention, two necks 22 are branched in opposite directions gently slanting upwardly from the upper end of the same stem 21 which rises upright from the substrate sheet 1, and two gently sloping approximately straight heads 23 project from the respective necks 22 in the same direction of branching of the necks 22, each head 23 having on its top 23a an arcuate surface arching in an extending direction.

Generally, an arcuate surface tends to slide on a sheet product due to its less friction as compared to a flat surface. Therefore, assuming that the top 23a of every head 23 is curved in the direction of branching of the necks 22, it tends to slip in the curving direction to make the skidproof device less resistant to skidding.

If the attaching surface of a companion sheet product is adequately soft and uneven, since two heads 23 of the individual engaging element 2 extend in opposite directions to slant gently upwardly, the distal end portion of the press-deformed individual head 23 pushes and deforms the attaching surface of the companion sheet product locally, when the skidproof device is pressed against the sheet product, so that mutual skidding of the skidproof device and the sheet product can be prevented as combined with the uneven attaching surface of the sheet product. If the attaching surface of a companion sheet product has piles or loops, in addition to preventing the relative skidding as described above, since the distal end portions of the individual heads 23 extending in sliding direction is caught by the piles or loops of the sheet product when the skidproof device is slid on the sheet product, further sliding can be prevented. Accordingly, even in the presence of the arcuate surface at the top 23a of every head 23, the skidproof device of this invention can give adequate resistance to skidding.

Since this arcuate surface at the top 23a of every head 23 gives the front surface of the skidproof device an improved touch which usually conflicts with the skidproof function, even if the engaging elements 2 come into contact with the skin, it is possible to prevent the user's skin from having any unpleasant feeling such as itchy feeling and being injured, or even being rough.

Further in the case that the sheet product has the flat or uneven surface, also if the attaching surface of the sheet product has piles or loops, even when the heads 23 are caught by the loops, the sheet product can be peeled off the skidproof device without difficulty because of the shape of the engaging elements 2, thus facilitating exchanging of the sheet product with a new one.

Further, since the whole skidproof device of this invention is made of synthetic resin, it is adequately durable so that, if used with an absorbing pad, a large-size paper diaper for patient or old person, which is expensive compared to that for infant, can be used several times.

According to this embodiment, detailed parameters of the engaging elements 2 are as follows: a thickness W1 of the engaging element 2 in the direction of branching of the heads 23 is 0.42 mm, a thickness W2 of the engaging element 2 in a direction perpendicular to the direction of branching of the heads 23 is 0.15 mm, an actual height H between the uppermost point O of the head 23 and the bottom surface of the recess 1a is 0.45 mm, a radius R1 of curvature of the convex arcuate surface at the top 23a of the head is 0.06 mm, a radius R2 of curvature of the concave arcuate surface at the branching portion 22a of the necks 22 is 0.03 mm, an angle θ between the oppositely branched necks 22 is 50°, a distance L1 between distal ends of the opposite heads 23 gently sloping upwardly from the same stem 21 is 0.6 mm, and a distance L2 between the centers of the adjacent stems 21 is 1.0 mm. The engaging elements 2 are arranged on the front surface of the substrate sheet 1 in such a manner that the composite projected area of the necks 22 and the heads 23 occupies about 25% of the entire front surface of the substrate sheet 1. In this embodiment, a depth D of the recesses 1a is 0.05 mm.

The parameters of the engaging elements 2 of this invention should by no means be limited to the foregoing values. Preferably, the thickness W1 of the engaging element 2 in the direction of branching of the heads 23 is within a range of 0.3–2 mm, and the thickness W2 of the engaging element 2 in a direction perpendicular to the direction of branching of the heads 23 is within a range of 0.1–1.5 mm. If the parameters are less than the lower limit values, the skidproof device is too soft and hence has not enough degree of resistance to skidding; while if the parameters exceed the upper limit values, the skidproof device is too rigid and hence gives the user an unpleasant touch. It is also preferable that the actual height H between the uppermost point O of the head 23 and the bottom surface of the recess 1a is within a range of 0.2–2.0 mm. Further, in order to obtain adequate softness and pleasant touch when the engaging elements 2 are pressed from the upper side, the radius R1 of curvature of the arcuate surface at the top 23a of the head 23 is preferably at least 0.04 mm and the radius R2 of curvature at the branching portion 22a of the neck 22 is at least 0.02 mm. In order to improve the softness, it is preferable that the individual head 23 has one or more local portions smaller in cross-sectional area than the remaining portions. If the angle θ between the oppositely branched necks 22 is within a range of 30°–120°, it is possible to avoid an itchy touch as combined with the adequate softness. Further, the density (number/cm$^2$) of the engaging elements 2 standing on the front surface of the substrate sheet 1 and having the above-mentioned parameters varies depending on the type of the companion sheet product and is preferably within a range of 4–720/cm$^2$ when considering the touch and the skidproofness as well as other factors all together.

In the foregoing embodiments, the individual engaging elements 2 of each row are laterally aligned with those of an adjacent row. Alternatively, the engaging elements 2 of a pair of adjacent rows may be arranged in a staggered pattern so that the substrate sheet 1 can be surely prevented from tearing transversely of the engaging element rows. In another alternative form, though it is not shown in the drawings, the engaging elements 2 distributed over the front surface of the substrate sheet 1 may be divided into a number of blocks in such a manner that the direction of branching of the heads 23 in each block is perpendicular to that in an adjacent block, thus making the skidproof device non-directive in resisting to skidding.

This skidproof device can be continuously molded in the following manner.

Figure 5:
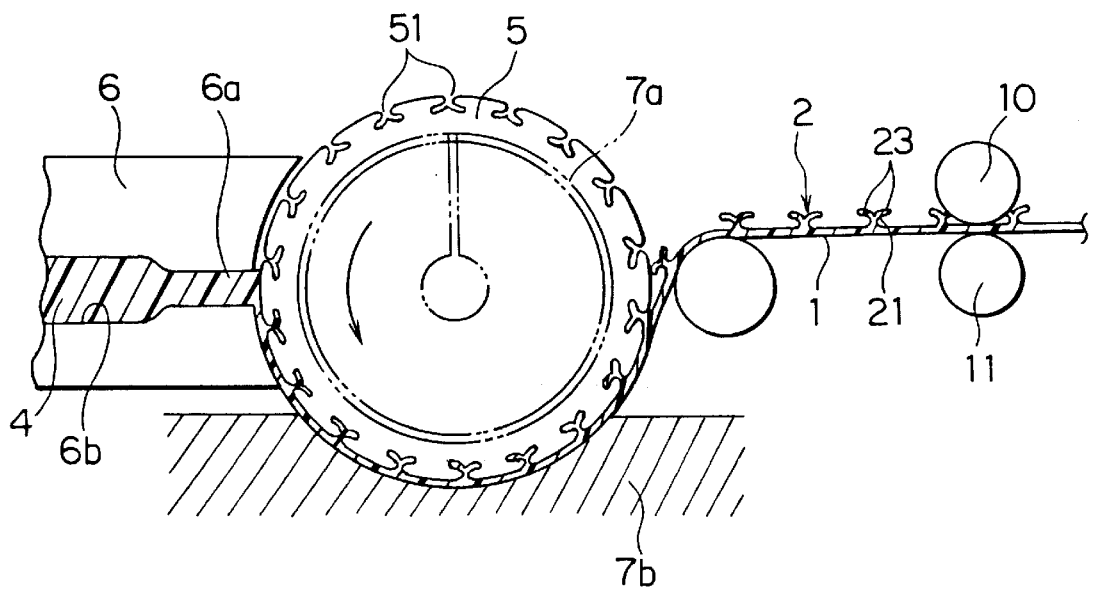
FIG. 5 is a fragmentary side view schematically showing a process in which the skidproof device of the invention is continuously molded.

FIG. 5 schematically shows an example of a continuous molding machine for the skidproof device of the invention, being partially enlarged. In FIG. 5, reference number 6 designates an extrusion nozzle whose tip has an arcuate surface substantially equal in curvature to a below-described die wheel 5 and which is disposed in confronting relationship with the die wheel 5 to define with the die wheel 5 a gap corresponding to the thickness of the substrate sheet 1 to be molded. This extrusion nozzle 6 is a T-type die which continuously extrudes molten resin 4 in a sheet form under a predetermined resin pressure and at a constant rate of flow from an orifice 6a disposed centrally in the arcuate surface of the tip. In this embodiment, a sprue 6b extends centrally through the extrusion nozzle 6.

The basic structure of the die wheel 5 is a hollow drum having a water cooling jacket 7a inside and composed of a number of annular plates placed one to another along the axis of the drum, as schematically shown in FIG. 5, and the die wheel 5 has a circumferential surface serving as a molding surface for a part of the skidproof device and spaced the above-described gap from the arcuate surface of the tip of the extrusion nozzle 6 with the axis die wheel 5 parallel to the orifice 6a. The circumferential surface of the die wheel 5 has a multiplicity of engaging-element-forming cavities 51, each bending in Y-shape inside the die wheel 5, arranged in a number of rows which are spaced at regular distances axially of the die wheel 5. Further, the circumferential surface of the die wheel 5 has a number of non-illustrated annular grooves extending circumferentially of the die wheel 5 and disposed one between each adjacent pair of rows of engaging-element-forming cavities 51. These annular grooves serve as cavities for molding part of the front surface of substrate sheet 1 which part exists beside the stems 21 and the heads 23. This die wheel 5 is driven by a non-illustrated conventional drive unit for rotation in the direction of an arrow in FIG. 5. Under the die wheel 5, a cooling water tank 7b is disposed in which about a lower half of the die wheel 5 is soaked.

In molding the molded skidproof device using this molding machine, when molten resin 4 continuously extruded under a predetermined resin pressure from the extrusion nozzle 6 is continuously introduced into the gap between the rotating die wheel 5 and the extrusion nozzle 6, part of the molten resin 4 is filled in the gap to mold the substrate sheet 1 and, at the same time, part of the molten resin is filled successively in the engaging-element-forming cavities 51, which are formed in the circumferential surface of the die wheel 5, to successively mold a multiplicity of engaging elements 2 on the front surface of the molded substrate sheet 1 as the die wheel 5 rotates.

As it revolves around a half of the circumferential surface of the die wheel 5, the molded skidproof device is positively cooled from the inside of the die wheel 5 by the water cooling jacket 7a and, at the same time, the molded skidproof device passes in the cooling water tank 7b, where low-temperature (about 15° C.) cooling water circulates to quickly cool the device, thereby facilitating solidification of the device. During that time, since the skidproof device is solidified by this quick cooling before crystallization progresses, the substrate 1 and the engaging elements 2 entirely have an adequate degree of softness. When the solidified substrate sheet 1 is drawn by a pair of take-up rollers 10, 11, the individual engaging element 2 having been cooled to become solidified in the engaging-element-forming cavity 51, which has a substantially Y shape, is smoothly removed off the cavity 51 as being deformed into a straight form. Soon after this removing, the engaging element 2 can only incompletely restore its original Y shape so that the two heads 23 of the engaging element 2 assume a higher posture, in which each head 23 extends at an angle slightly upright from the stem 21, as compared to the generally Y shape of the cavity 51.

This angle of the head 23 with respect to the stem 21 is different between the case it is in a direction same as the direction in which the die wheel 5 rotates and the case it is in a reverse direction. One head 23 extending forwardly of the engaging-element-forming cavity 51 is subject to a larger removing resistance as compared to the other head 23 extending backwardly. It is accordingly understood that the forwardly extending head 23 slants upwardly by a larger angle as compared to the backwardly extending head 23.

It is understood from this phenomenon that, if slanting angles $\alpha 1$, $\alpha 2$ of forward and backward head-forming portions of the cavity 51 with respect to the horizontal plane are preset differently when designing, the forward and backward heads 23 of the engaging element 2 having been removed off the die wheel 5 will assume the same slanting angle with respect to the horizontal plane.

Figure 7:
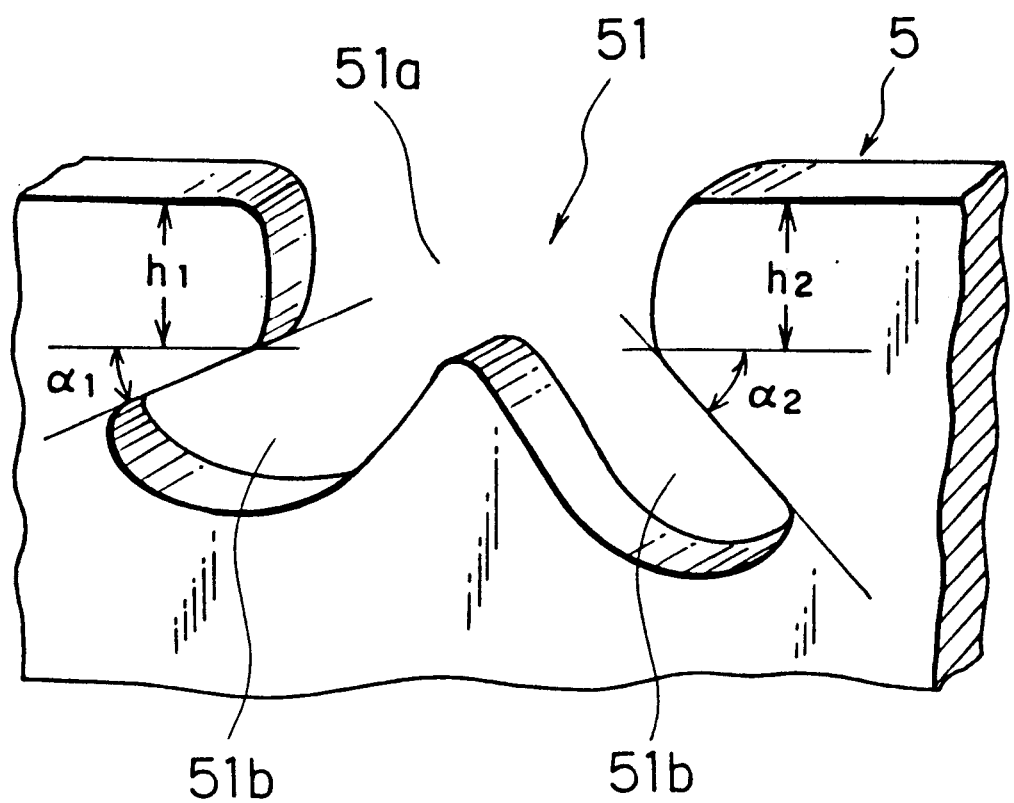
FIG. 7 is a fragmentary perspective view of a die wheel, showing a preferred example of shape of engaging-element-forming cavities.

FIG. 7 schematically shows a preferred shape of the engaging-element-forming cavity 51. It is preferable that the slanting angle $\alpha 1$ is within a range of $-5°-+80°$ while the slanting angle $\alpha 2$ is within a range of $+10°-90°$. Also preferably, the ratio between the height h1 and h2 from the circumferential surface to the start point of slanting between a stem-forming cavity 51a extending radially from the circumferential surface of the die wheel 5 and a head-forming cavity 51b is within a range of 1:0.1–1:1.50. Practically, of course, the slanting angle and the height ratio vary depending on the material to be used and should not be limited to the above-mentioned values though they should not be far from these. According to the illustrated example, the slanting angle $\alpha 1$ of the forward head-forming cavity 51b is 10°, the height h1 of the stem-forming cavity 51a is 0.20 mm, the slanting angle $\alpha 2$ of the backward head-forming cavity 51b is 27, and the height h2 of the stem-forming cavity 51a is 0.23 mm.

For peeling the skidproof device of this invention off the die wheel 5, the vertical pair of take-up rollers 10, 11 rotatable in opposite directions in synchronism with each other is used. Though the circumferential surfaces of the take-up rollers 10, 11 may be smooth, it is preferable that the circumferential surface of each take-up roller 10, 11 is covered by an elastomeric layer, as of soft urethane, so that the engaging elements 2 can be prevented from inadvertently damaged.

Figure 6:
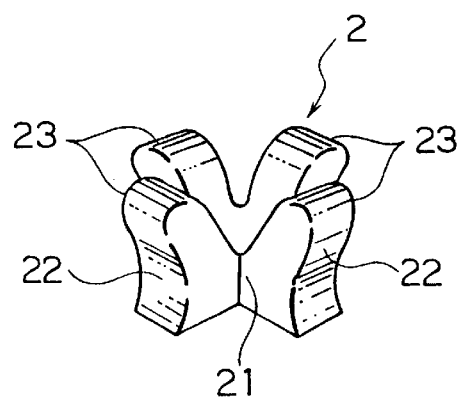
FIG. 6 is a perspective view showing a modified engaging element of still another skidproof device according to a third embodiment.

In the foregoing embodiments, each engaging element 2 has the pair of oppositely branched heads 23. The number of the branched heads 23 should by no means be limited to two; for example, according to a third embodiment shown in FIG. 6, each engaging element 2 may have four heads 23 branched in a crisscross manner from a single stem 21 whose cross-sectional shape is crisscross. For molding the skidproof device having the engaging elements 2 according to the third embodiment, though there is no illustration in the accompanying drawings, a single row of engaging elements 2 may be molded on a set of five annular plates, for example. One annular plate has in its circumferential surface first cavities each for molding the half of a stem 21 circumferentially and also a pair of heads 23 extending in opposite circumferential directions from the deep end of the stem half, two annular plates sandwiching the first annular plate has in its circumferential surface second cavities for molding the remaining half of the stem 21 extending parallel to the axis of the die wheel, and the remaining two annular plates sandwiching the foregoing three annular plates has in their circumferential surfaces third cavities for molding the other pair of heads 23 extending axially in opposite directions. These five plates are place one to another, with these cavities being aligned, to form the die wheel with which the above-described operation is performed to mold the devices.

According to the skidproof device of this invention, since each of a plurality of substantially straight heads 23 extending in different directions from a single stem 21 of the individual engaging element via the same number of necks 22 has an upwardly convex arcuate surface, it is possible to improve the touch of the heads 23. If the neck 22 and/or the individual head 23 is locally slightly smaller in cross-sectional area perpendicular to the center line than the remaining portions, it is possible to increase the softness so that a further improved touch can be realized. Further, since the individual engaging element 2 has at the branching portion 22a of the necks 22 an upwardly concave arcuate surface, it is possible to prevent the engaging element 2 from tearing at the branching portion 22a when the engaging element 2 is pressed from the upper side, thus increasing the durability.

Assuming that the skidproof device is sandwiched between a sanitary pad and a paper diaper, the plural heads 23 branched in different directions from the single stem 21 is pressed against the pad to catch piles or small loops standing on the pad, thus effectively preventing the pad from skidding in any direction. With this skidproof device, unlike the conventional skidproof device in which hooks engage, it is possible to peel the pad off the skidproof device comfortably without damaging the skidproof device and the diaper as well, thus making the diaper adequately durable to repeated use.

What is claimed is:

1. A synthetic resin skidproof device that is comfortable to the touch and has a durable structure, comprising:

(a) a substrate sheet; and
   (b) a multiplicity of skidproof engaging elements molded on a front surface of said substrate sheet and adapted to be mated with a companion sheet product, each of said skidproof engaging elements being composed of a single stem, at least two necks branched and sloping upwardly from an upper end of said stem, and at least two heads extending one from an upper end of each of said necks with an upward slope, each of said heads having on its top an upwardly convex arcuate surface, each of said heads extending from a respective one of said necks in a direction continuously away from said substrate sheet.

2. A synthetic resin skidproof device according to claim 1, wherein each of said skidproof engaging elements has at a branching portion of said necks a concave arcuate surface, and the center line of each of said heads is curved upwardly.

3. A synthetic resin skidproof device according to claim 1, wherein a thickness W1 of said stem of each said skidproof engaging element in a direction of branching of said necks is 0.3–2.0 mm, a thickness W2 of said necks of each said skidproof engaging element in a direction perpendicular to the direction of branching is 0.1–1.5 mm, a height H between said front surface of said substrate sheet and an uppermost point O of each said head is 0.2–2.0 mm, and a distance L1 between respective distal ends of said heads branched in opposite directions from the same stem is 0.4–3.8 mm.

4. A synthetic resin skidproof device according to claim 1, wherein the number of said heads of each said skidproof engaging element is two which are directed in opposite directions.

5. A synthetic resin skidproof device according to claim 1, wherein a radius R1 of curvature of said arcuate surface of said top of each said head is at least 0.04 mm, a radius R2 of curvature of said arcuate surface of said branching portion of said necks of each said skidproof engaging element is at least 0.02 mm.

6. A synthetic resin skidproof device according to any one of claims 1–5, wherein an angle θ between said necks branched oppositely from the same stem is 30°–120°.

7. A synthetic resin skidproof device according to any one of claims of 1–5, wherein a density of said skidproof engaging elements on said front surface of said substrate sheet is 4–720/cm$^2$.

8. A synthetic resin skidproof device according to any one of claims 1–5, wherein said substrate sheet has in said front surface a multiplicity of recesses, said skidproof engaging elements rising upwardly from bottom surfaces of said recesses.

* * * * *